United States Patent [19]

Helke

[11] Patent Number: 4,586,390
[45] Date of Patent: May 6, 1986

[54] NOZZLE FOR THE CONTINUOUS SEPARATION OF A REPRESENTATIVE SAMPLE FROM A DUST-BEARING GAS FOR ITS ANALYSIS

[75] Inventor: Risto J. A. Helke, Tampere, Finland

[73] Assignee: Oy Tampella AB, Tampere, Finland

[21] Appl. No.: 668,963

[22] Filed: Nov. 7, 1984

[30] Foreign Application Priority Data

Nov. 17, 1983 [FI] Finland .................................. 834210

[51] Int. Cl.⁴ .............................................. G01N 1/24
[52] U.S. Cl. ............................. 73/864.73; 73/863.81; 73/863.58; 73/864.33
[58] Field of Search ........... 73/864.73, 864.33, 863.58, 73/863.81, 863.21, 863.83, 863.84, 864.74

[56] References Cited

U.S. PATENT DOCUMENTS

| | | | |
|---|---|---|---|
| 1,994,884 | 3/1935 | Chew ............................ | 73/864.33 X |
| 2,682,277 | 6/1954 | Marshall et al. ............. | 73/864.33 X |
| 3,107,535 | 10/1963 | Kraftson . | |
| 3,198,265 | 8/1965 | Voelkerding ................ | 73/864.74 X |
| 3,559,491 | 2/1971 | Thoen .......................... | 73/863.21 X |
| 3,786,682 | 1/1974 | Winter et al. ................ | 73/864.33 X |
| 4,032,395 | 6/1977 | Burnette ...................... | 73/864.73 X |
| 4,044,612 | 8/1977 | Powell ......................... | 73/864.74 X |
| 4,335,539 | 10/1982 | Schotz ......................... | 73/864.73 X |
| 4,392,387 | 6/1983 | Izumi ........................... | 73/863.21 |
| 4,479,379 | 10/1984 | Tarcy ........................... | 73/863.58 X |

FOREIGN PATENT DOCUMENTS 1808886 4/1970 Fed. Rep. of Germany .
1006965 3/1983 U.S.S.R. .......................... 73/863.21

Primary Examiner—Stewart J. Levy
Assistant Examiner—Tom Noland
Attorney, Agent, or Firm—Roylance, Abrams, Berdo & Goodman

[57] ABSTRACT

The invention relates to a nozzle for continuous separation of a representative sample from a duct-containing gas for its analysis. The nozzle has a pipe, intended to open into the sample-taking space, for continuous separation of the sample from a dust-containing gas and for directing the sample to be analyzed, and a second pipe for feeding water into the mouth of the sample-taking pipe in order to keep it clean and to mix the water with the gas sample. In order to obtain a representative sample and to ensure that the nozzle remains open, at the sample-taking end of the sample-taking pipe there is fitted a sleeve which extends somewhat beyond the pipe and encircles it, the water pipe being connected to the sleeve in order to feed water via the annular clearance between the sleeve and the sample-taking pipe to a point in front of the mouth of the sample-taking pipe, and from the inner wall of the open part of the sleeve, extending beyond the sample-taking end of the sample-taking pipe, there extends a ring-like stop oriented against the water flow, in which case a slit, transverse in relation to the gas flow direction and encircling the sample-taking mouth, is formed between the stop and the end of the pipe.

10 Claims, 8 Drawing Figures

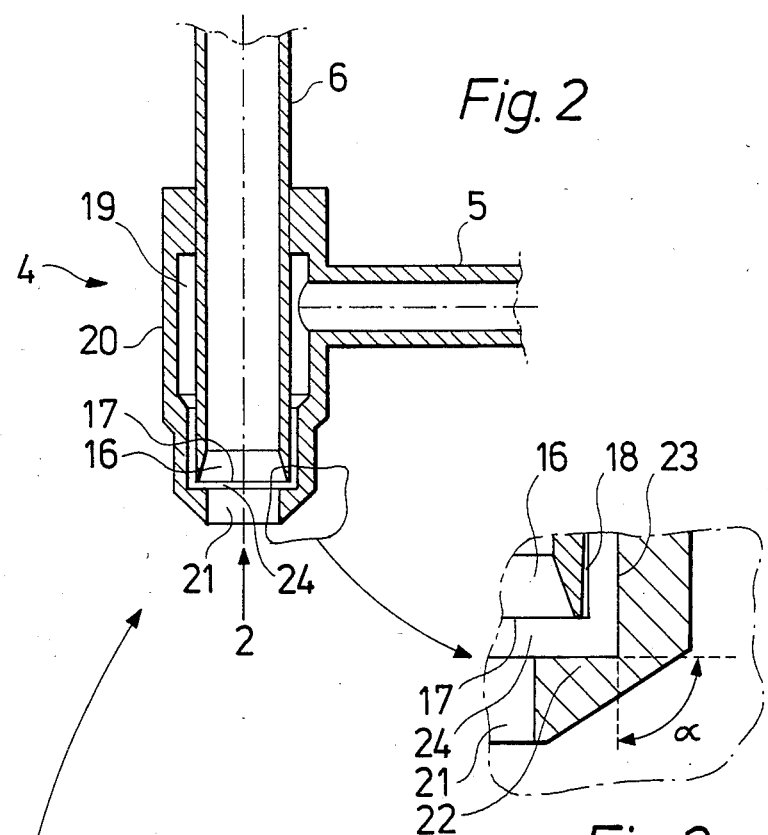
Fig. 2
Fig. 3
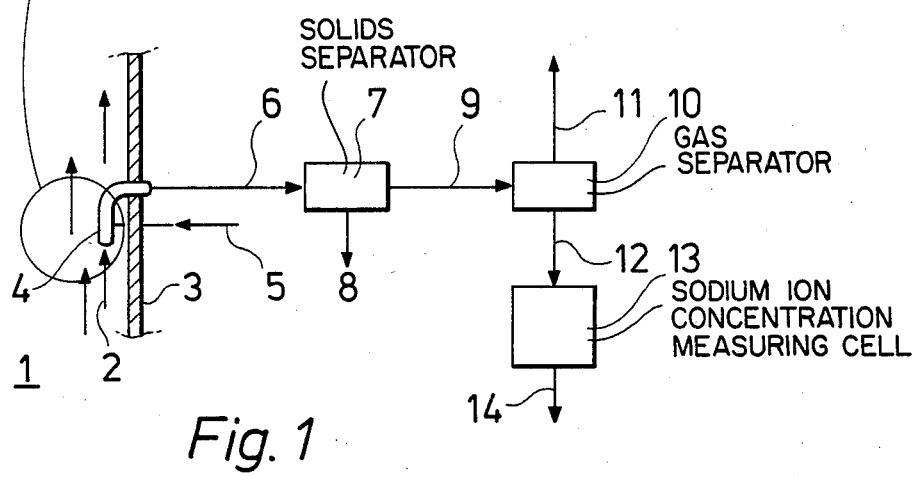
Fig. 1

NOZZLE FOR THE CONTINUOUS SEPARATION OF A REPRESENTATIVE SAMPLE FROM A DUST-BEARING GAS FOR ITS ANALYSIS

BACKGROUND OF THE INVENTION

The present invention relates to a nozzle for separating a representative sample from a gas mixture which contains a finely divided solid, in order to analyze the sample, the nozzle having a sample-taking mouth opening into the sample-taking chamber and a conduit connected to it, for separating a sample and for directing it to analysis, and a second conduit for feeding liquid into the said sample-taking mouth in order to clean it and to mix the liquid with the gas sample.

Previously known is an oxygen analyzer provided with a so-called rotating spray probe, in which the probe consists of a pipe opening into the sample-taking space and equipped with a water-cooled mantle, and in which there is additionally a second pipe for feeding water from the tip of the probe in the direction of the gas sample, mixed with the sample. Water is sprayed in front of the sample-taking pipe, whereupon part of the water is mixed with the sample gas flowing into the probe and part of it washes the mouth of the probe clean of the dust which had adhered to it. Thus such a probe cannot be used for absorbing solid or gas into water when it is desired to make a quantitative analysis of the gas or solid content of the gas sample or suspension. The purpose of the water spray used in the sample-taking probe of such an oxygen analyzer is only to keep the mouth of the sample-taking pipe open when a sample is being taken from dust-bearing flue gases. The concentration of oxygen is measured from a dried and purified gas sample, in which case the quantity of the water used for keeping the sample-taking probe open is not significant with respect to the analysis.

The object of the present invention is thus to provide a nozzle for separating a representative sample from a dust-bearing gas for analysis, the nozzle having a sample-taking mouth opening into the sample-taking chamber, and a conduit connected to it for separating the sample and for directing it to analysis, and a second conduit for feeding a liquid, preferably water, into the said mouth of the sample-taking pipe in order to keep it clean and to mix the liquid with the gas sample, all the washing liquid being recovered carefully so that the solid and gaseous constituents dissolved in it from the gas can be analyzed quantititively. Since the analysis is carried out on the washing liquid, and not on the dried and purified gases as in the above-mentioned prior known sample-taking appartus, it is very important that all of the washing liquid is recovered quantitatively while ensuring that the sample-taking probe remains open.

In the specification and patent claims of the Application, by the analysis of the gas mixture which contains a possibly dust-containing solid is meant the analysis of the gaseous components of the gas mixture and/or its various solid constituents in dust-like form. By the gas mixture, respectively, is meant a combination which contains at minimum two gaseous substances or at minimum one gaseous substance and at minimum one solid.

SUMMARY OF THE INVENTION

The objectives and advantages mentioned above are achieved in such a way that the second conduit, for feeding liquid, includes at least one slit-like conduit part transverse to the central axis of the sample-taking mouth of the sample-taking conduit and situated around the said central axis, and from this part the liquid which keeps the mouth clean and mixes the gas is fed into the mouth transversely to the flow direction of the gas from around substantially the whole mouth. In practice this is achieved simply by fitting at the sample-taking end of the sample-taking pipe a substantially concentric sleeve, extending somewhat beyond it, and the liquid pipe is connected to this sleeve in order to feed liquid via the clearance or clearances between the sleeve and the sample-taking pipe to a point in front of the mouth of the sample-taking pipe, there extending inwards from the inner wall of that sleeve part which extends beyond the sample-taking end of the sample-taking pipe a ring-like stop oriented transversely to the gas flow, the slit-like conduit part being formed between the stop and the end of the sample-taking pipe.

The angle between the longitudinal axis of the sample-taking pipe and the ring-like stop oriented transversely to the gas flow and inwards from the inner wall of the open sleeve part which extends beyond the sample-taking end of the sample-taking pipe is preferably about 90° in relation to the gas flow, so that at the mouth of the sample-taking pipe there is formed a liquid film or liquid drop spray which covers as well as possible the entire cross sectional area of the pipe and, owing to the suction prevailing in the sample-taking pipe, effectively mixes with the gas flow.

When measured axially, the slit between the sample-taking end of the sample-taking pipe and the ring-like stop of the sleeve, oriented against the gas flow, is preferably 0.005–0.1 mm in width, for example approximately 0.05 mm. The slit between the sample-taking end of the sample-taking pipe and the ring-like stop must be continuous and maximally even, so that a drop spray or flim which covers maximally well the cross sectional area of the sample-taking mouth of the sample-taking pipe will be formed. The slit is preferably adjustable, for example so that the sleeve is fitted to the sample-taking pipe in such a way that it can be transferred axially, and is then locked in place in relation to the sample-taking pipe. The sleeve and the sample-taking pipe can be locked in relation to each other by means of, for example, a locking ring or some other suitable method, while keeping a fitting plate in the slit during the locking.

The sample-taking pipe and the sleeve are preferably concentric in order to produce a symmetric slit or slit-like conduit part, and thus a maximally symmetric liquid spray in the sample-taking pipe, and between them there is preferably a continuous clearance having a ring-like cross section.

The diameter of the opening formed by the ring-like stop of the sleeve is preferably at maximum equal to the inner diameter of the sample-taking pipe, in certain cases even somewhat smaller than its inner diameter.

Liquid, under pressure, is fed into the preferably annular space between the sleeve and the sample-taking pipe via the second conduit. The longitudinal axis of the second conduit is preferably perpendicular to the longitudinal axis of the sleeve and the sample-taking pipe. Moreover, the second conduit may tangentially intersect with the annular space.

DESCRIPTION OF THE DRAWINGS

FIG. 1 depicts schematically a gas analysis apparatus provided with a nozzle according to the invention, FIG. 2 depicts a cross sectional side view of the probe of FIG. 1, on a larger scale, FIG. 3 is a cross sectional partial representation of the probe of FIG. 2, on a slightly still larger scale.

DESCRIPTION OF THE PREFERRED EMBODIMENTS

Figure 4:
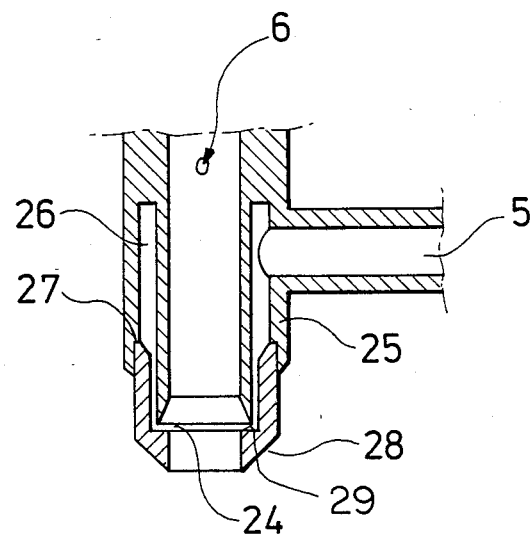
FIG. 4 depicts one embodiment of the probe according to the invention.

In FIG. 1, the flue gas conduit is indicated by 1. Sample gas 2 is sucked in at a certain rate through a sample-taking probe 4 according to the invention. The inner surface of the probe 4 is washed with a continuous liquid spray, the liquid in general being water. Water is directed via pipe 5 to the sample-taking end of the sample-taking probe 4, so that all the water passes inside the sample-taking probe 4 in order to wash the sample gas with water and to rinse the inner surface of the probe with a precisely measured water quanitity, which is thereafter directed along pipe 6 to a separating device 7, in which the solid constituents 8 which have not dissolved in the water are separated from the water flow 9, which is directed to the subsequent separating device 10, in which the gases 11 are separated from the water flow 12 and are pumped away. The water flow 12 is directed into a measuring cell 13, in which the concentration of sodium ions is measured continuously by means of a sodium ion specific electrode. The concentration of sodium ions as electrode potential is observed with the aid of a plotter. By using the sample gas volume 2, the washing liquid volume 5 and the measured sodium ion concentration it is possible to calculate the concentration of glauber salt in the flue gases at any given moment. These can all be determined by well known means.

Finally the water flow 14 is directed to the drain or back into the process.

As is seen in greater detail in FIG. 2, the sample-taking probe, indicated in general by reference numeral 4, consists of a sample-taking pipe 6 having at its sample-taking end 17 a sample-taking mouth 16 opening into the sample-taking space. At the sample-taking end 17 of the sample-taking pipe 6 there is fitted a sleeve 20 which extends somewhat beyond it and encircles it, and to which the water pipe 5 has been connected in order to feed water into the annular clearance 19 between the sleeve 20 and the sample-taking pipe 6, and from there further, via the annular slit between the outer wall 18 of the sample-taking end 17 of the sample-taking pipe 6 and the inner wall 23 of the sleeve, to a point in front of the mouth 16 of the sample-taking pipe 6, as seen in greater detail in FIG. 3. In order to direct the water flow to a point in front of the mouth 16 of the sample-taking pipe 6, there is in that part of the sleeve which extends beyond the end 17 of the sample-taking pipe 6 a ring-like stop 22 which is oriented inwards from the inner wall 23, transversely to the gas flow, this stop 22 forming an angle $\alpha$ with the central axis of the sample-taking mouth 16 of the sample-taking pipe 6. This angle $\alpha$ is 90° in the embodiment shown in the drawing, but it can be smaller or larger.

The dimension of the slit between the sample-taking end 17 of the sample-taking pipe 6 and the ring-like stop 22 of the sleeve 20 is relatively critical, and it must, when measured axially, be in the order of 0.005–0.1 mm, and preferably about 0.05 mm when water is used as the rinsing liquid.

As seen in greater detail in FIG. 3, the diameter of the opening 21 formed by the ring-like stop 22 of the sleeve 20 is smaller than the inner diameter of the sample-taking pipe 6, a factor which is advantageous although not necessary.

Figure 8:
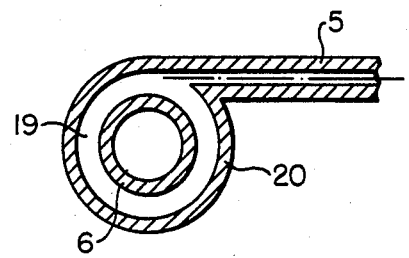
FIG. 8 is a top cross-sectional view of the embodiment of the probe illustrated in FIG. 1.

The longitudinal axis of conduit 5 is perpendicular to the longitudinal axes of sleeve 20 and pipe 6. In the embodiment illustrated in FIG. 8, conduit 5 tangentially intersects annular clearance 19. The nozzle according to the present invention enables a continuous quantitative analysis of dust-bearing gas to be carried out, since all of the absorption liquid used can be measured and, furthermore, it is ensured that the probe remains open. If, for example, under conditions more difficult than normal it seems that, nerveless, the probe tends to get clogged, the sample-taking can be interrupted momentarily whereupon the water flow discharging from the slit 24, when the suction prevailing in the sample-taking pipe 6 during sample taking is interrupted, is directed outwards from the nozzle into the sample-taking space and effectively cleans the mouth 16 of the sample-taking pipe 6 and the opening 21 formed by the ring-like stop 22 of the sleeve 20. Such a short-time wash can be carried out sequentially so that the tip of the nozzle will not get soiled. When the suction of the sample into the sample-taking pipe 6 is resumed, its quality is immediately correct, since the entrance of both the gas sample and of the washing liquid into the sample-taking pipe 6 have been interrupted during the above-mentioned sequential cleaning.

In terms of the functioning of the invention it is advantageous that the liquid is sprayed into the nozzle at a point as close as possible to the front edge of the nozzle so that the part of the sample-taking conduit which tends to get soiled will be as short as possible. For this reason it is advantageous to make the stop 22 of the sleeve 20 as thin as possible in the axial direction, at least at that edge which is toward the sample-taking mouth.

By means of the invention described above, a nozzle is obtained wherein, inside the sample-taking pipe, there is formed, as close as possilbe to the sample inlet, a liquid film against which the gas and the dust contained in the gas impinge and immediately begin to dissolve in the liquid.

After passing through the nozzle, when flowing with the gas in the pipe 6, the washing liquid forms plugs appearing at rather regular intervals and thus rinses the pipe walls well, forming a large absorption surface for the gas and the solid contained in it.

According the FIGS. 2 and 3, there is, between the sleeve 20 and the sample-taking pipe 6, an annular clearance 19, along which the liquid is fed to a point in front of the nozzle. In practice the nozzle can also be constructed so that on the outer surface of the sample-taking pipe or on the inner surface of the sleeve there are longitudinal grooves which extend to the tip of the sample-taking pipe or to the stop of the sleeve. In this case, when the sleeve is in place, there would not be any annular clearance between the nozzle and the sleeve but there would be only longitudinal conduits. The diameter of the longitudinal conduits is preferably carefully selected so that the slit 24 still has a throttling effect on the water passing through slit 24. Stated differently, the conduits are preferably designed such that the water pressure in the conduits is less than in slit 24 so that throttling of the water in slit 24 is greater than the throttling of the water in the longitudinal conduits. This assures that slit 24 will deliver an unbroken "film" of water into pipe 6.

It is possible to construct the nozzle also in other ways. Instead of the sleeve structure it is possible to use, for example, the solution according to FIG. 4.

FIG. 4 shows part of the nozzle end, the nozzle frame being indicated by numeral 25. The nozzle frame has a sample-taking conduit 6 which runs all the way to the front of the frame. Around the sample-taking conduit 6 at the front end of the frame 25 there is formed an annular groove 26, to which the conduit 5, directing the rinsing and absorbing substance, is connected. At the front end of the frame there is installed a threaded cap-like piece 28, which is attached to the frame 25 either on the circumference of the frame or, as in FIG. 4, by means of threading provided in the ring-like groove 26. In this case the clearance of the nozzle, i.e. the axial width of the slit 24, can be easily set by shaping the cap-like pieces in such a way that they have a fixed mating surface which engages the frame at, for example, the mating surface of the frame at the point indicated by 27 and, respectively, a limiting surface 29 coming in alignment to the slit 24 situated at some distance in relation to the mating surface in the axial direction. By making the axial distance between the mating surface and the limiting surface 29 different in the different pieces 28, the clearance can be adjusted easily without any precise measuring work, when the difference between the distance between the mating surface in the frame and the end surface of the frame, and respectively the mating surface of the cap-like piece and the limiting surface in each piece, are known.

Figure 5:
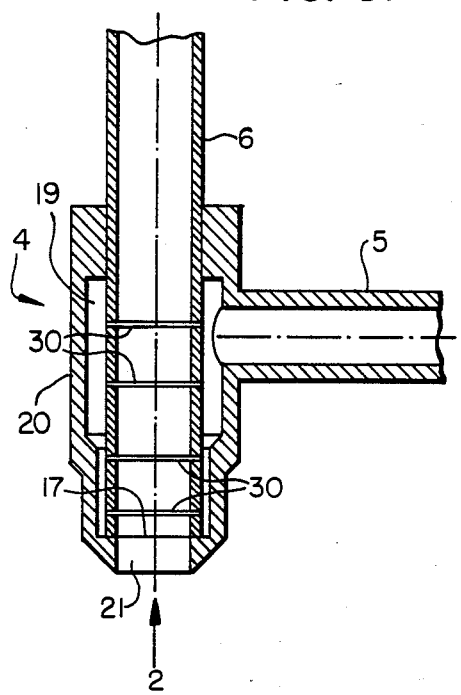
FIG. 5 is a cross-sectional side view of a second embodiment of the probe of this invention.
Figure 6:
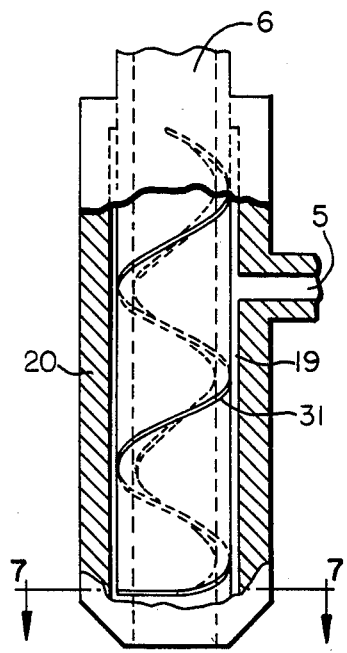
FIG. 6 is a cross-sectional side view of a third embodiment of the probe of this invention.
Figure 7:
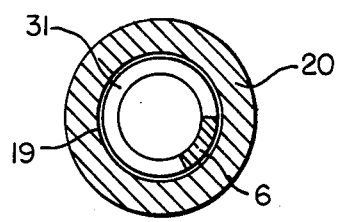
FIG. 7 is a cross-sectional view taken along line 7—7 of FIG. 6.

The operation of the nozzle according to the invention can under some conditions be further improved by providing spaced ring slits 30 in a sample-taking conduit 6 (see FIG. 5) successively in the axial direction of the sample-taking conduit, in which case the corresponding number of liquid films are produced, which promotes mixing. In this case it is also possible to use narrower slits and thus thinner water films. Instead of the ring-like slit 24 it is, of course, also possible to use a slit which forms a gently rising spiral in conduit 6, such as spiral slit 31 in FIGS. 6 and 7 which encircles the sample-taking mouth at least once. Thereby a continuous liquid film which covers the cross sectional area of the conduit is formed, as seen in the axial direction of the sample-taking conduit. When using a spiral slit it is possible, by using a suitable structure and a suitable material, to adjust the width of the slit by compressing or stretching the spiral in the axial direction. In the variations depicted above it is, of course, preferable that the first slit, or the beginning of the spiral slit, is as close as possible to the edge of the sample-taking mouth so that the edge will not get considerably soiled.

Slit-like conduit parts 24 can also be combined, for example by fitting first a ring-like conduit part and thereafter a spiral-like conduit part, or vice versa, or in some other way. The parts of the conduit can be parallel to each other in such a way that the water films formed have the same orientation in relation to the central axis of the nozzle. The slit-like conduit parts can also have different orientations in relation to each other, in which case the water films are respectively in different orientations in relation to the central axis.

What is claimed is:

1. A nozzle for separating a representative sample from a gas mixture which contains a finely divided solid, in order to analyze it, the nozzle comprising a sample-taking mouth which opens into a sample-taking space, a first conduit connected to it for separating the sample and for directing it to the analysis; and a second conduit for feeding liquid into the sample-taking mouth in order to clean it and to mix the liquid with the gas sample, the second conduit, for feeding the liquid, including at least one slit-like conduit part transverse to the central axis of the sample-taking mouth of the sample-taking conduit, situated around the central axis, the liquid which keeps the mouth clean and is mixed with the gas being fed through this conduit part into the mouth, transversely to the gas flow direction and from around substantially the entire opening.

2. A nozzle according to claim 1, in which there are at least two of the slit-like conduit parts.

3. A nozzle according to claim 1, in which at least one slit-like conduit part has a spiral shape.

4. A nozzle according to claim 1, in which at least one of the slit-like conduit parts has a ring-like shape.

5. A nozzle according to claim 4, in which the conduit comprises a sample-taking pipe, and that one slit-like conduit part is formed with the aid of a sleeve fitted at the end of the sample-taking pipe and extending somewhat beyond the pipe end in the axial direction of the sample-taking mouth, the sleeve having a ring-like stop extending from its inner surface towards its central axis, in which case the sleeve is fitted in such a way that in the axial direction the stop is at a distance from the end of the sample-taking pipe and the said slit-like conduit part is formed between the stop and the sample-taking pipe.

6. A nozzle according to claim 5, comprising between the sleeve and the sample-taking pipe at least one clearance which communicates with the slit-like conduit part and is integral with the conduit for feeding the liquid.

7. A nozzle according to claim 1, in which at least one slit-like conduit part is at each point substantially perpendicular to the central axis of the sample-taking mouth.

8. A nozzle according to claim 1, in which at least one slit-like conduit part has a constant width in the longitudinal direction of the sample-taking pipe.

9. A nozzle according to claim 1, in which the width of each slit-like conduit part is 0.005–0.1 mm, the width being the dimension thereof which is parallel to the central axis of the sample taking mouth.

10. A nozzle according to claim 1, in which each slit-like conduit part is positioned substantially symmetrically in relation to the central axis of the sample-taking mouth.

* * * * *